United States Patent
Wang et al.

(10) Patent No.: US 8,350,213 B2
(45) Date of Patent: Jan. 8, 2013

(54) CHARGED PARTICLE BEAM DETECTION UNIT WITH MULTI TYPE DETECTION SUBUNITS

(75) Inventors: Joe Wang, Campbell, CA (US); Xu Zhang, Cupertino, CA (US); Zhongwei Chen, San Jose, CA (US)

(73) Assignee: Hermes Microvision Inc., Hsin-Chu (TW)

( * ) Notice: Subject to any disclaimer, the term of this patent is extended or adjusted under 35 U.S.C. 154(b) by 480 days.

(21) Appl. No.: 12/715,766

(22) Filed: Mar. 2, 2010

(65) Prior Publication Data

US 2011/0215241 A1    Sep. 8, 2011

(51) Int. Cl.
*H01J 37/26*    (2006.01)
(52) U.S. Cl. ............ 250/310; 250/396 R; 250/396 ML
(58) Field of Classification Search .................. 250/310, 250/397, 396 R, 396 ML
See application file for complete search history.

(56) References Cited

U.S. PATENT DOCUMENTS

| | | | |
|---|---|---|---|
| 5,644,132 A * | 7/1997 | Litman et al. | 250/310 |
| 7,449,690 B2 * | 11/2008 | Nishiyama et al. | 250/310 |
| 7,960,697 B2 * | 6/2011 | Chen et al. | 250/310 |
| 8,217,363 B2 * | 7/2012 | Hatano et al. | 250/396 ML |

* cited by examiner

*Primary Examiner* — Kiet T Nguyen
(74) *Attorney, Agent, or Firm* — Stout, Uxa, Buyan & Mullins, LLP (57) ABSTRACT

A detection unit of a charged particle imaging system includes a multi type detection subunit in the charged particle imaging system, with the assistance of a Wien filter (also known as an E×B charged particle analyzer). The imaging system is suitable for a low beam current, high resolution mode and a high beam current, high throughput mode. The unit can be applied to a scanning electron inspection system as well as to other systems that use a charged particle beam as an observation tool.

16 Claims, 7 Drawing Sheets

CHARGED PARTICLE BEAM DETECTION UNIT WITH MULTI TYPE DETECTION SUBUNITS

FIELD OF THE INVENTION

The present invention generally relates to a detection unit of a charged particle imaging system, and more particularly to a multi-detector in the charged particle imaging system.

BACKGROUND OF THE INVENTION

In order to lower the costs and improve the performance of ICs (integrated circuits), the design nodes of ICs should be made smaller. Shrinking of the design nodes to 22 nm or even smaller, however, makes the defect inspection tool, such as an optical system, less able to detect the defects, owing to the optical resolution of light sources used being equal to or larger than the defect dimension. For advancing resolution in defect inspection, a more applicable inspection tool, such as an e-beam inspection tool, is provided for semiconductor process inspections. Further, in a VC (voltage contrast) mode of inspection the e-beam inspection tool can inspect for under-layer defects, the performance of which is almost impossible for current-day optical inspection systems to match. Hence, the e-beam inspection tool has become more important in the context of semiconductor processes.

Nevertheless, due to restrictions of the e-beam system per se, throughput thereof is much lower than that of optical systems. In order to increase throughput and VC inspection, larger currents, such as several hundreds nano-amperes (nA), are applied in the e-beam inspection systems. On the other hand, to increase the inspection resolution of the e-beam inspection system, small currents, such as several tens of pico-amperes (pA), are applied instead.

Up to the present day, there still is no single e-beam system that can handle both large current and small current inspections. A suitable means of using different e-beam systems for variant purposes while inspecting would definitely require more space (at least double the space) and more costs for the inspection. Therefore, there is a need for a new design of an e-beam inspection tool having the capability to handle both the large and small beam currents for handling both high resolution and high speed requirements.

BRIEF SUMMARY OF THE INVENTION

One of bottle necks for using e-beam inspection system to handle both high resolution and high throughput is the detection system in the e-beam inspection tool. The detection unit has to handle a large dynamic range of signal current from several tens of pico-amperes (pA) to several hundred nano-amperes (nA). Previously, there has been no such detection unit in an e-beam inspection system with the capability. This type of operation needs a large dynamic signal current range for the detection system in the tool. The present invention generally relates to a detection unit of a charged particle imaging system, more particularly to an in-lens detection unit, with a multi type detector subunit, in the charged particle imaging system, with the assistance of a Wien filter (also known as an ExB charged particle analyzer). The present invention provides an imaging system that is suitable for both a low current, high resolution mode and a high current, high throughput mode. Merely by way of example, the invention has been applied to a scanning electron beam inspection system. It should be recognized, however, that the invention can apply to other systems using charged particle beams as observation tools.

One embodiment of the present invention integrates a solid state detector and an E-T detector into one detection unit to collect signal electrons for a charged particle beam imaging system.

According to another embodiment of the present invention, the signal electron is directed to a solid state detector section or an E-T detector section by a Wien filter, also known as an ExB charged particle analyzer, according to the high resolution mode, or the high beam current mold setting.

In another embodiment of the present invention, the detection unit is divided into more than one section. Each section of the detection unit can be a solid state detector or an E-T detector coated with different scintillant material according to the required detector gain. A neutral density filter can be configured to each section of the detection unit to reduce the intensity of received light during imaging. The signal electrons are directed to a predetermined section of the detection unit by a Wien filter.

DETAILED DESCRIPTION OF THE INVENTION

Reference will now be made in detail to specific embodiments of the invention. Examples of these embodiments are illustrated in the accompanying drawings. While the invention will be described in conjunction with these specific embodiments, it will be understood that it is not intended to limit the invention to these embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations are not described in detail in order not to obscure unnecessarily the present invention.

The present invention generally relates to a detection unit of a charged particle imaging system, and more particularly to an in-lens detection unit, with a multi type detection subunit, in the charged particle imaging system, with the assistance of a Wien filter (also known as an E×B charged particle analyzer). The present invention provides an imaging system that is suitable for both a low current, high resolution mode and a high current, high throughput mode. Merely by way of example, the invention has been applied to a scanning electron beam inspection system. It will be recognized, however, that the invention can apply to other systems using a charged particle beam as an observation tool.

A semiconductor photo diode (SPD) detector is widely used in semiconductor e-beam inspection systems, such as, for example, in U.S. Pat. Nos. 6,392,231, 6,605,805 and 6,960,766, along with US Patent Publications 20080121810 and 20090294664, due to its capability to handle large signal current and its simple structure. The SPD detector, also called a solid state diode detector, operates on the principle of electron-hole pair production induced in a semiconductor by energetic electrons. The electronic structure of a semiconductor consists of an empty conduction band separated by a band gap of forbidden energy states from the filled valence band. When energetic electrons scatter inelastically in the semiconductor, some electrons are promoted to the conduction band, each leaving the absence of an electron, or hole, in the valence band. Through the mechanism of electron-hole production, the SPD acts to raise the signal by the energy of the signal electrons. A current amplifier is required, preferably of the operational amplifier type. The gain of the SPD detector is directly tied to the energy of signal electrons, and can handle very large beam current (up to mA level), because of lower energy signal the gain of the detector is low compared with MCP and PMT types detectors. A detailed description can be obtained by reference to the publication by Joseph I. Goldstein et al., Scanning Electron Microscopy and X-Ray Microanalysis, $2^{nd}$ edition, published by Plenum, 1992, Chapter 4.

The detector which collects small signal current for the charged particle imaging system can be a traditional Everhart-Thornley (E-T) detector, also known as a photo multiplier tube detector (PMT). The E-T detector performs very well for a conventional small signal current e-beam imaging system such as a laboratory used SEM, the detector being described further with reference to, for example, the same publication, on page 177. The typical gain range of the photomultiplier, between about $10^3$ and $10^6$, is adjustable by selecting the voltage on the electrodes. The PMT can have difficulty outputting signal electron currents larger than 0.1 μA due to dynode restriction; high speed inspection requirement is almost impossible.

Another detector, called a micro channel plate (MCP), is a planar component used for detection of charged particles, such as electrons or ions, and impinging radiation (ultraviolet radiation or X-rays). It is closely related to an E-T detector, as both intensify single particles or photons by the multiplication of electrons via secondary emission. However, similar to the PMT detector, the MCP detector can have difficulty outputting signal electron currents larger than 0.1 μA. A more detailed description can be obtained also by referring to the same publication, chapter 4.

Figure 1:
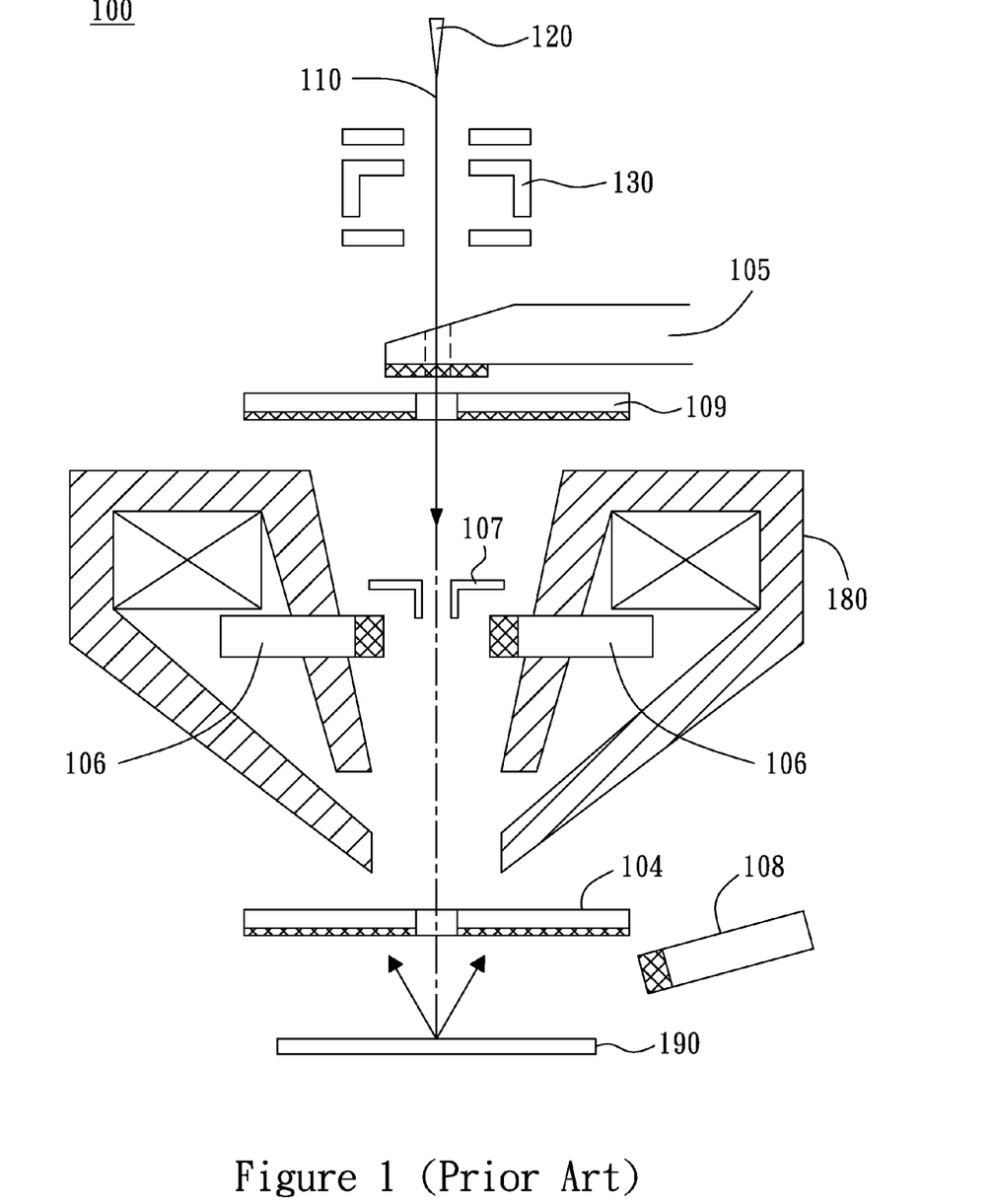
FIG. 1 is a schematic diagram that showing variant prior-art detector units located at different positions in a charged particle imaging system.

These variant detectors can be applied to different locations in a scanning charged particle imaging system as shown in FIG. 1, which schematically diagrams such variant detection units (e.g., as published in previous patents and publications) located at different positions relative to an objective lens 180 of a scanning charged particle imaging system.

According to the arrangement in the figure, a charged particle beam 110 is emitted from a charged particle emitter (tip) 120 through gun lens unit 130 and objective lens 180 to a surface of specimen 190 with a beam shield 107 within the objective lens 180.

Most scanning charged particle imaging systems have a backscattered-electron detector 104, which may be an SPD detector as described, for example, in the same publication, page 184. It may also be a PMT detector as disclosed by Cowham in U.S. Pat. No. 6,211,525. The charged particle imaging systems also have a side detector 108 used for secondary electron detection as described, for example, in the same publication, page 177, and as also disclosed by Ishikawa in U.S. Pat. No. 4,818,874, wherein an E-T detector is used as the side detector 108. Both of these two types of detectors 104 and 108 are close to specimen 190 and out of the column or charged particle beam 110.

Both detector 105 and detector 109 are located at the top of objective lens 180. The detect 105 above the objective lens 180 is disclosed by Kella et al. in U.S. Pat. No. 6,545,277, in which a scintillator receives secondary electrons scattered from the specimen and generates photons. A light guide is coupled to the scintillator and a photomultiplier tube to receive photons for conversion to an electron current signal by the photomultiplier tube.

The detector 109 above the objective lens 180, which is of a general, known design nowadays, is disclosed by many patents and publications, such as Frosien et al. in U.S. Pat. No. 4,831,266, Shariv in U.S. Pat. No. 6,236,053, Kochi et al. in U.S. Pat. No. 7,067,808, Petrov et al. in U.S. Pat. No. 7,233, 008, and Shemesh et al. in US Patent Publication 20060054814, in which Frosien et al. teaches that the detector 109 can be of either a PMT type or an SPD type while Shariv teaches that the detector 109 can be of an MCP type. Further, the detector 109 can be segmented as taught by Frosien et al., Shariv, and Shemesh et al.

Another objective lens type of detector 106 in the objective lens 180 is disclosed by Yonezawa in U.S. Pat. No. 6,617,579, in which the detector used can be of an MCP type or a SPD type and segmented in two portions.

All detector units disclosed above are dedicated to a single type of detector at one location, such as detector 104 or detector 109 in FIG. 1. No prior-art reference teaches a multi-sectional detector or detection unit with a multi type detection subunit or different detector types to handle different types of signals with the help of a Wien filter. Even to the extent some prior art may be interpreted to teach the use of a multi section, the purpose of such technology would appear to be to depict a stereo image, entailing of course the same type detector with a multi channel arrangement.

The present invention, by using a Wien filter, incorporates different types of detectors (multi section) in a single detection unit. Instead of imaging on different sections (or multi channels) simultaneously, the Wien filter is used to guide the signal electrons to only one section (or single channel) detector. A Wien filter, also known as an E×B charged particle analyzer, is a superimposed orthogonal magnetic and electrostatic field. By altering the magnetic field and the electrostatic field strength and direction, a charged particle moving in this superimposed field will alter its moving direction accordingly.

Figure 2:
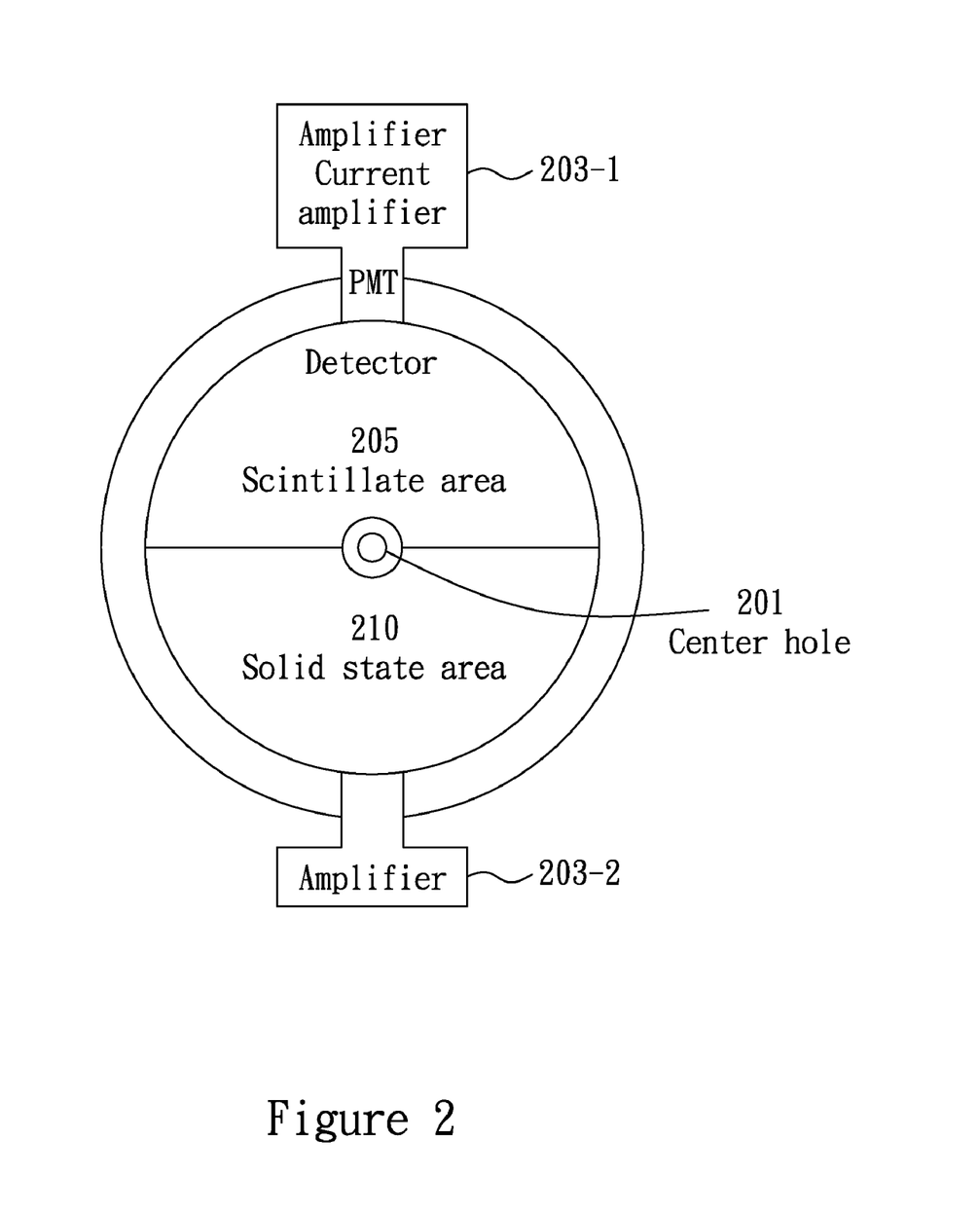
FIG. 2 is a diagrammatic representation of an example of a multi in-lens detection unit according to an embodiment of present invention.

One embodiment of the present invention introduces a mixed in-lens on-axis multiple detector system. FIG. 2 shows a plan view of the mixed in-lens multiple detector system 200 which integrates two types of detectors into one detection system. A scintillate detector area 205 is for high resolution requirements, and a solid states detector area 210 is for high signal beam current requirements. The detector system 200 has a center hole 201 to let the primary beam pass through. The received signal will be amplified by an amplifier 203-1 from the scintillate detector area 205 or by an amplifier 203-2 from the solid states detector area 210 and then output to an image processing unit (not shown). The amplifier 203-1 is a photon multiplier tube and a current amplifier for the scintillate detector area 205, and the amplifier 203-2 is a current amplifier for the solid state detector area 210. During an imaging process, an image processing unit in the control computer will process the signals collected from a preset detector area only. If the system 200 is undergoing (e.g., in) a high resolution inspection mode, the SE and BSE emanating from the specimen surface are directed to the scintillate detector area by a Wien filter. If the system 200 is undergoing, for example a VC mode, then the SE and BSE emanating from the specimen surface are directed to the solid state detector area by the Wien filter.

Figure 3A:
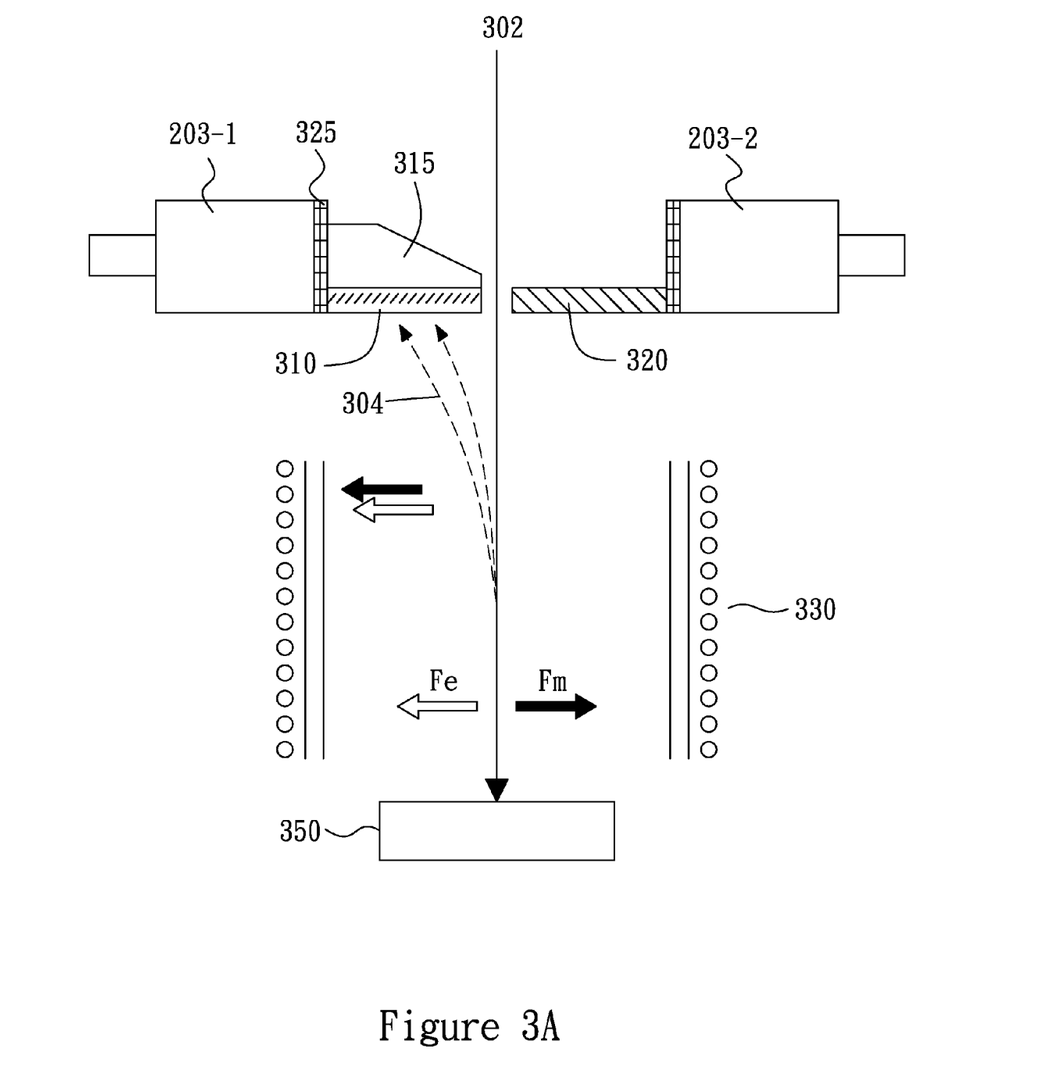
FIG. 3A is a diagrammatic representation of signal electrons trajectory that have been directed to scintillator detector area of the detection system by an ExB charged particle analyzer according to an embodiment of present invention.
Figure 3B:
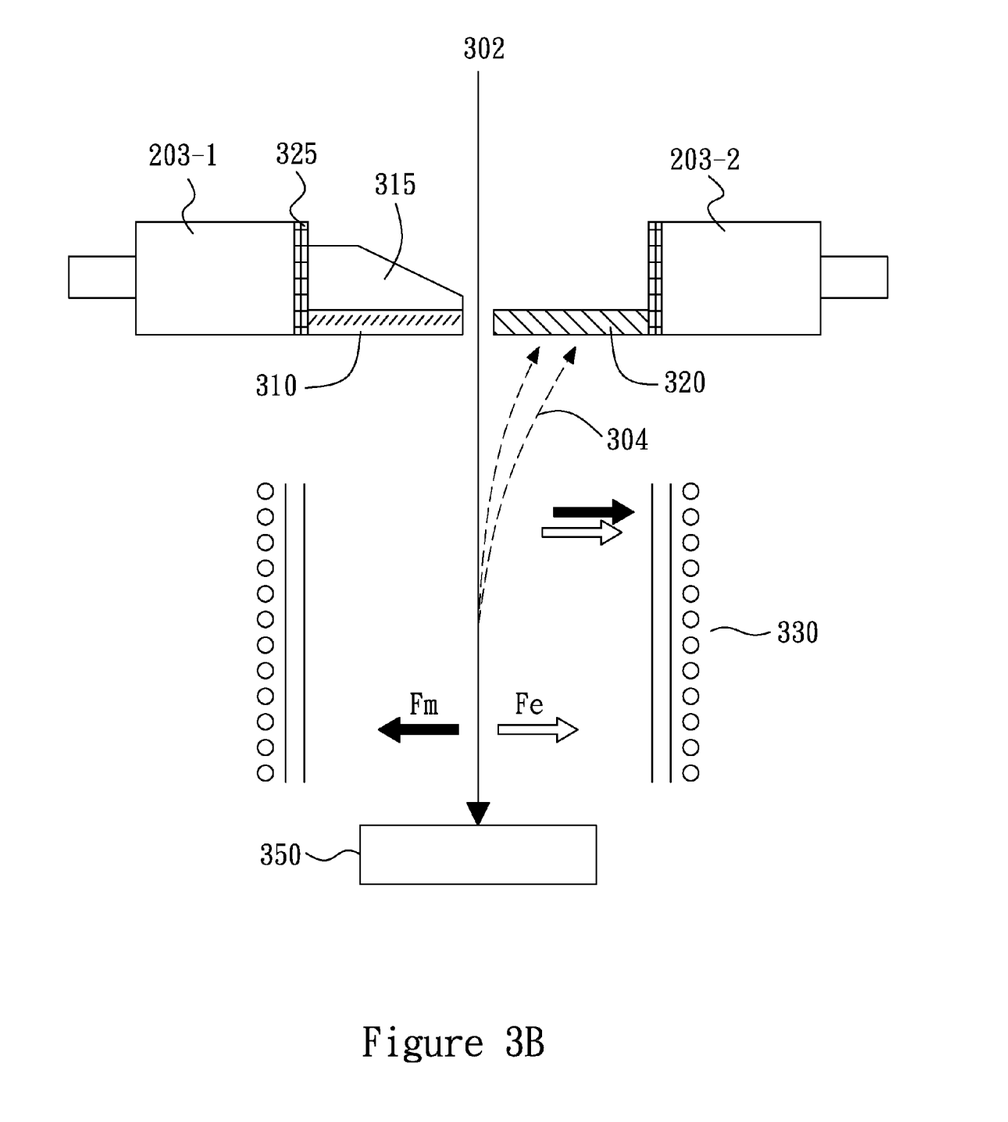
FIG. 3B is a diagrammatic representation of signal electrons trajectory that have been directed to solid state detector area of the detection system by an ExB charged particle analyzer according to an embodiment of present invention.

The superimposed magnetic field strength (Fm) and electrostatic field strength (Fe) of the Wien filter 330 in FIG. 3A that are used to divert the emanating electrons are pre-calculated by the control computer according to the primary beam energy or a user's decision/direction. FIG. 3A illustrates a cross-sectional view of the electrons being diverted to the scintillate detector 310 by the Wien filter 330, and FIG. 3B illustrates in a cross-sectional view the secondary and back-scattered electrons being diverted to the SPD detector 320 by the Wien filter 330. The incoming signal electrons will hit the phosphor coated surface and generate light signal as shown in FIG. 3A. The signal photons pass through light guide 315 in FIG. 3A and reach photomultiplier tube (PMT) 203-1, the signal then going to image processing unit (not shown) for high resolution purposes. Between the light guide 315 and PMT 203-1, a neutral density filter or ND filter 325 may be configured to/for each detection channel of the detection unit. The function of the ND filter 325 is to reduce the light of all wavelengths or colors equally. With the ND filter 325, the PMT can keep the optimized gain without overloading when large beam current or a VC mode is selected. Further, the incoming signal electrons may hit the SPD detector 320 guided by the Wien filter 330 shown in FIG. 3B and generate signal electrons. The signal electrons pass through the amplifier 203-2 and then go to image processing unit (not shown) for handling of the large signal current.

Figure 4:
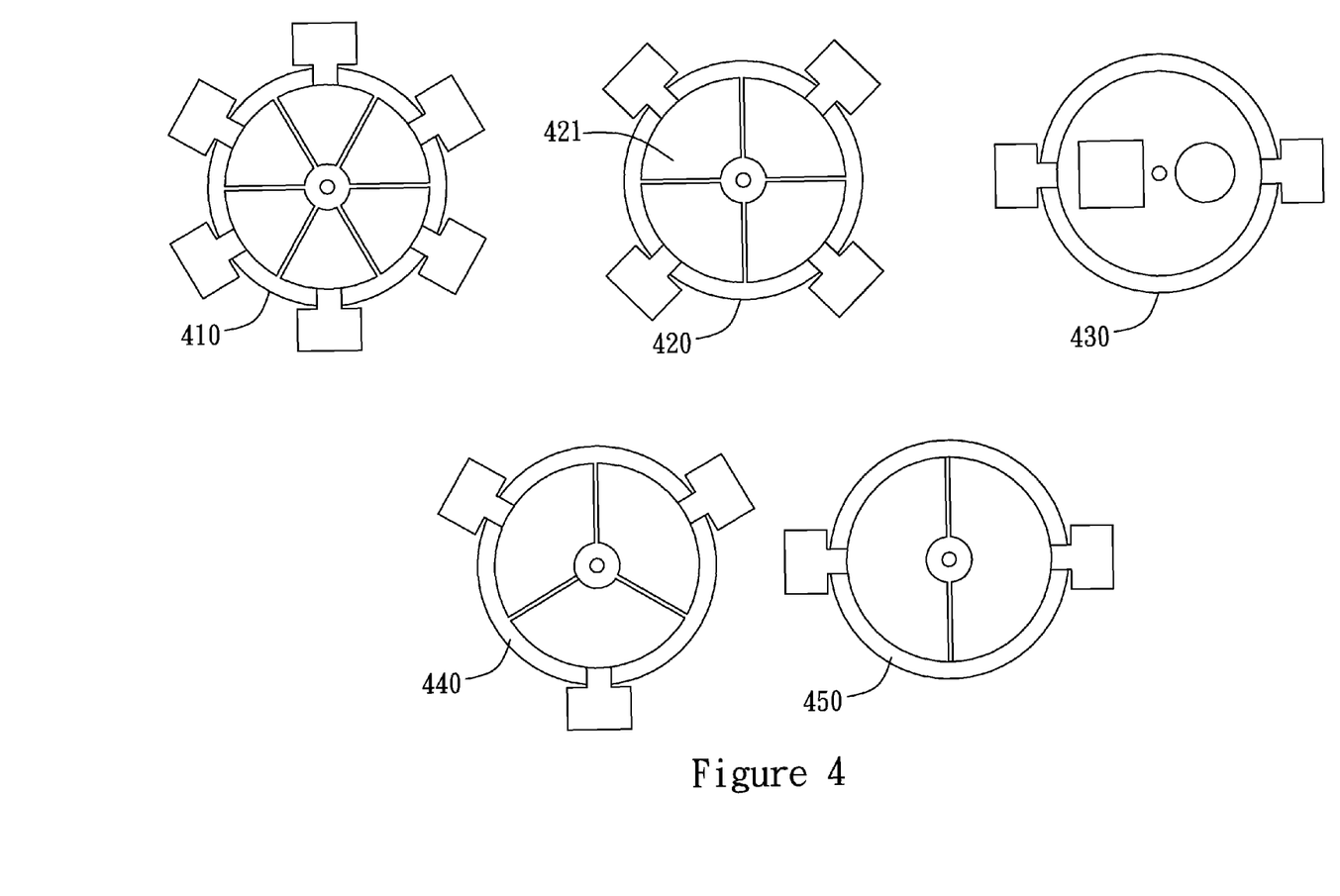
FIG. 4 is a diagrammatic representation of examples of different sections of an in-lens detector subunit according to an embodiment of present invention.

FIG. 4 illustrates some examples of different designs of an in-lens on-axis detection unit, with a multi type detection subunit. The multi detector can be divided into many detecting areas for different purposes. Examples can include six sections detector 410, four sections detector 420, two sections detector but with different shape of the detecting area 430, three sections detector 440, and regular two sections detector 450. All of these multi detectors have a central bore to let the primary beam pass through. Each section of the detector is independent but shares a single imaging detection channel. The image is not a combination of the signal received from other detection sections. The secondary electrons and backscattered electrons are guided by the Wien filter from the specimen surface and directed to a pre-set detection section. Thus, the image of a specimen is formed by only one detection section of the quadruple detector 420, for example. The detection section that the Wien filter directs all signal electrons from specimen surface to is pre-set according to the characteristic of the inspection.

Figure 5:
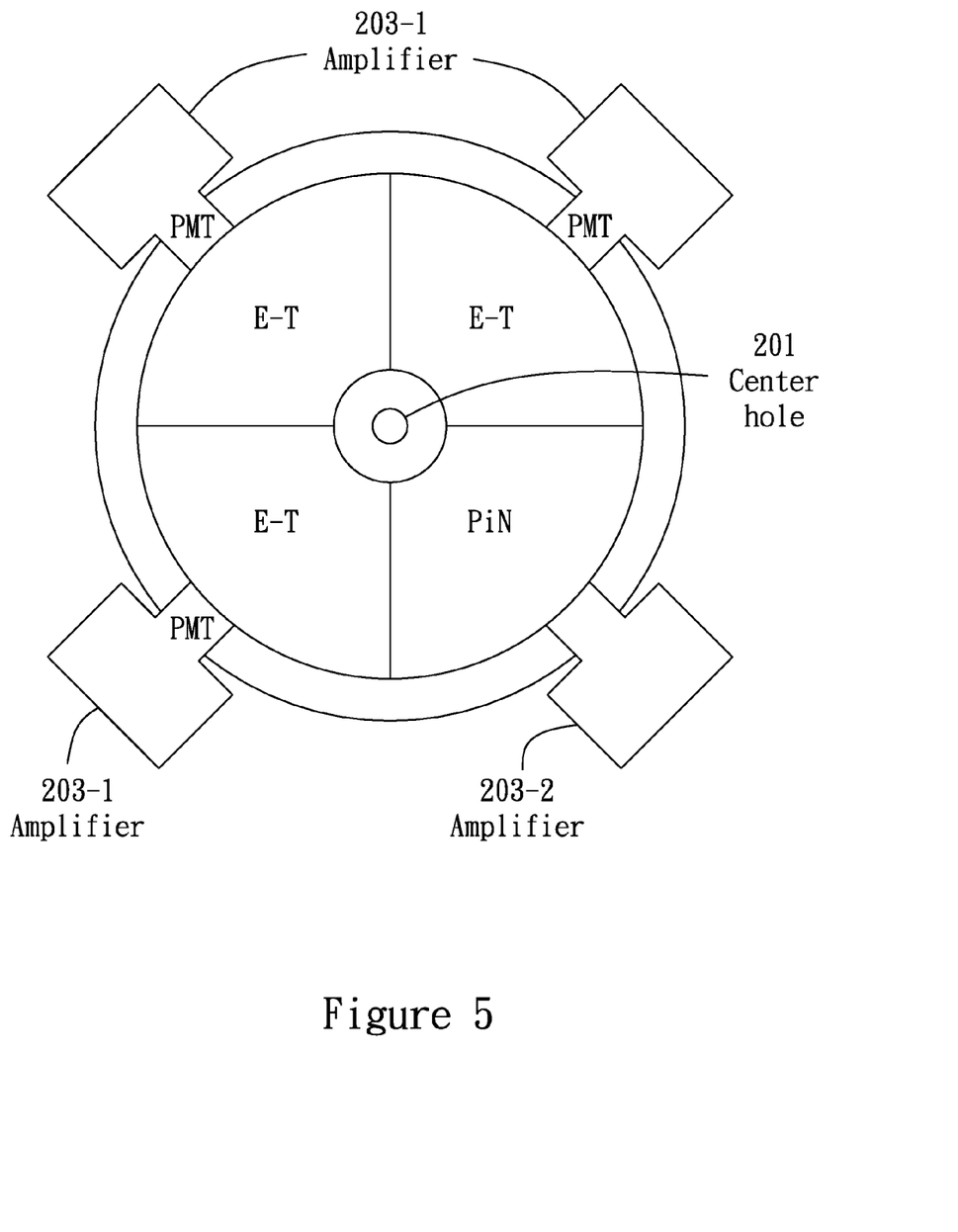
FIG. 5 is an example of a quadrupole in-lens detector according to an embodiment of present invention. The detector sub-systems have 3 E-T detectors that coated with different scintillate material and one solid state detector.

Another embodiment of the present invention discloses a mixed in-lens quadruple detector with 3 E-T detection sections and 1 SPD detection section as illustrated in FIG. 5. Again, each of the 3 E-T detection sections can be coated with a different scintillate material for different utilization and configuration of an ND filter between the light guide and PMT. The SPD is configured to handle larger beam current (several hundreds nanoamperes) or VC mold imaging. The Wien filter can direct the signal electrons emanating from the specimen surface to one specified detection section when an inspection imaging mold is accordingly selected.

The present in-lens, on-axis detection unit, which comprises a multi type detection subunit and which utilizes a Wien filter to direct signal electrons to the detection subunit, can be applied to any other system that utilizes a charged particle beam as an imaging tool. The unit can be used with systems/tools such as a scanning electron microscope (SEM), a modified SORIL (Swing Objective Retarding Immersion Lens) SEM, a transmission electron microscope (TEM), and a focused ion beam (FIB) system used for substrate inspection or metrological purpose.

Theoretically, an in-lens, on-axis detection unit, with a multi type detection subunit, can be symmetrically distributed around the primary beam. Those detectors can use different amplifiers, or can share one or more amplifiers. The multiple detectors can be one type of detector, such as in a configuration of all scintillator detectors, but with different filters or with different phosphor coatings. It can also be mixed with different types of detectors, such as in the case of a mix of one or more each of scintillator detectors and SPD detectors. The other types of detectors, such as MCP detectors, also can be involved in the detection system.

Figure 6:
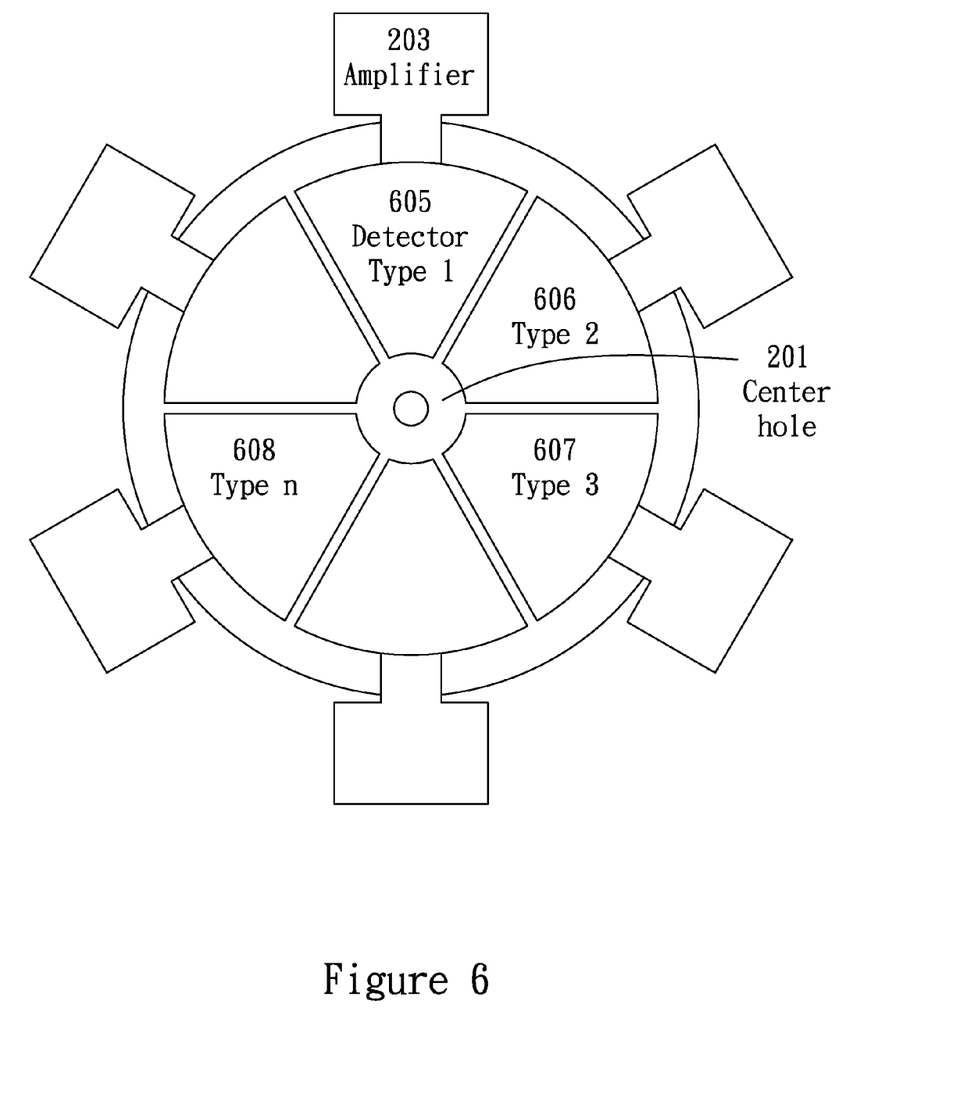
FIG. 6 is another diagrammatic representation of examples of different configurations of n different in-lens detector subsystems according to an embodiment of present invention.

There is no limitation to the number of detectors for the invented in-lens, on-axis detection unit as FIG. 6 illustrates. One may configure n different detection sections in one in-lens, on-axis detection unit, wherein n is a number greater than 1. The detector sub-systems can be different in type, different in detecting material, and/or of different filters. For example the detection sections 605, 606, 607, and 608 contain different types of detectors.

Although the multi detector system has multiple detectors, however, it is not a multiple channel imaging system because the image is not a combination result of other detection sections in image processing. Each section cannot work simultaneously. The present system uses the signal from only one detection section to form an image.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A method for imaging a specimen surface by directing signal charged particles to a specified detection area, the method comprising:
   providing a charged particle beam system to irradiate primary charged particles onto the specimen surface;
   providing a detection unit which includes a multi type detection subunit to receive the signal, charged particles emanating from the specimen surface, wherein the detection unit has at least two subunits for different detection purposes;
   providing an E×B charge particle analyzer to direct signal charged particles emanating from the specimen surface to one of the two subunits by a control computer, wherein the control computer calculates superimposed magnetic field strength and electrostatic field strength of the E×B charge particle analyzer that diverts the signal charged particles; and generating images based on detected signal particles received by the detection unit.

2. The method of claim 1, wherein the detection unit which includes a multi type detection subunit has at least one solid state detector.

3. The method of claim 1, wherein the detection unit which includes a multi, type detection subunit has at least one of an E-T detector and a PMT detector.

4. The method of claim 1, wherein the detection unit which includes a multi type detection subunit is positioned inside a column, and the subunit is symmetrically distributed around the primary charged particle beam.

5. A system for inspecting a specimen utilizing a charged particle beam, the system comprising:
a charged particle imaging system arranged to provide a specimen surface image;
a detection unit which includes a multi type detection subunit coupled to receive signal charged particles emanating from a surface of the specimen, wherein the detection unit has at least two subunits for different detection purposes;
an E×B charge particle analyzer constructed to direct signal charged particles emanating from the specimen surface to one of the subunits; and
a control computer configured to set and calculate superimposed magnetic field strength and electrostatic field strength of the E×B charge particle analyzer that diverts the signal charged particles.

6. The system of claim 5, wherein the detection unit which includes a multi type detection subunit has at least one solid state detector.

7. The system of claim 5, wherein the detection unit which includes a multi type detection subunit has at least one of an E-T detector and a PMT detector.

8. The system of claim 5, wherein the detection unit which includes a multi type detection subunit is an in-lens detector and is positioned inside a column of the charged particle beam system.

9. A detection unit of a charged particle imaging system, comprising:
a first sub detection unit for handling larger signal currents;
a second sub detection unit with high gain, wherein the first sub detection unit and the second sub detection unit are configured in or on an objective lens of the charged particle imaging system to receive signal charged particles from a specimen to be detected, and wherein a center hole is configured between the first sub detection unit and the second sub detection unit to allow a primary beam of the charged particle imaging system to pass therethrough to the specimen; and
an E×B charge particle analyzer between the specimen and the first sub detection unit as well as the second sub detection unit, wherein the signal charged particles are controlled by the E×B charge particle analyzer, and the E×B charge particle analyzer directs the signal charged particles to the first sub detection unit or the second sub detection unit.

10. The detection unit of claim 9, wherein the first sub detection unit is a semiconductor photodiode detector, and the second sub detection unit is an E-T detector.

11. The detection unit of claim 10, wherein the E×B charge particle analyzer is a Wien filter.

12. The detection unit of claim 11, further comprising one sub detection unit.

13. The detection unit of claim 11, further comprising two sub detection units.

14. The detection unit of claim 13, wherein the four sub detection units use different scintillate material.

15. The detection unit of claim 9, wherein the charged particle imaging system is a scanning electron microscope (SEM), a transmission electron microscope (TEM), or a focused ion beam (FIB) system.

16. The detection unit of claim 15, wherein the SEM is a modified SORIL SEM.

* * * * *